United States Patent
Subbaraman et al.

(10) Patent No.: US 6,294,571 B1
(45) Date of Patent: Sep. 25, 2001

(54) METHOD FOR USING NEEM EXTRACTS AND DERIVATIVES FOR PROTECTING WOOD AND OTHER CELLULOSIC COMPOSITES

(75) Inventors: Ramesh B. Subbaraman, Fullerton; Barry R. Brucker, Beverly Hills, both of CA (US)

(73) Assignee: Independent Ink, Inc., Gardena, CA (US)

( * ) Notice: Subject to any disclaimer, the term of this patent is extended or adjusted under 35 U.S.C. 154(b) by 0 days.

(21) Appl. No.: 09/151,264

(22) Filed: Sep. 11, 1998

(51) Int. Cl.$^7$ .......................... A01N 43/16; A01N 43/08; A01N 65/00
(52) U.S. Cl. .......................... 514/453; 422/1; 424/195.1; 424/413; 424/DIG. 10; 424/DIG. 11; 428/540; 428/541; 514/468; 514/531; 514/919
(58) Field of Search .................... 514/453, 468, 514/531, 919; 424/195.1, 413, DIG. 10, DIG. 11, 405; 422/1; 428/540, 541

(56) References Cited

U.S. PATENT DOCUMENTS

| | | | | | |
|---|---|---|---|---|---|
| 4,486,475 | * | 12/1984 | Shutov et al. | ........................ | 427/351 |
| 4,556,562 | | 12/1985 | Larson | ................ | 424/195.1 |
| 4,902,713 | | 2/1990 | Rembold et al. | ................. | 514/453 |
| 4,943,434 | | 7/1990 | Lidert | ................. | 424/195.1 |
| 4,946,681 | | 8/1990 | Walter | ................. | 424/195.1 |
| 4,960,791 | | 10/1990 | Klocke et al. | ........................ | 514/468 |
| 5,001,146 | | 3/1991 | Carter et al. | ........................ | 514/453 |
| 5,001,149 | | 3/1991 | Klocke et al. | ........................ | 514/468 |
| 5,047,242 | | 9/1991 | Klocke et al. | ........................ | 424/195.1 |
| 5,110,591 | | 5/1992 | Williams | ................. | 424/195.1 |
| 5,124,349 | | 6/1992 | Carter et al. | ........................ | 514/453 |
| 5,281,618 | | 1/1994 | Walter | ................. | 514/453 |
| 5,298,247 | | 3/1994 | Godrej et al. | ................. | 424/195.1 |
| 5,352,672 | | 10/1994 | Staetz et al. | ................. | 514/65 |
| 5,352,697 | | 10/1994 | Butler et al. | ........................ | 514/468 |
| 5,372,817 | | 12/1994 | Locke et al. | ........................ | 424/405 |
| 5,391,779 | | 2/1995 | Lidert | ................. | 514/453 |
| 5,395,951 | | 3/1995 | Nagasampagi et al. | ............. | 549/383 |
| 5,397,571 | | 3/1995 | Roland et al. | ........................ | 424/405 |
| 5,843,215 | * | 12/1998 | Whalon et al. | ................... | 106/18.29 |
| 6,060,075 | * | 5/2000 | Rao et al. | ............................. | 424/405 |

FOREIGN PATENT DOCUMENTS

| 39 12 059 | * | 10/1990 | (DE) . |
| 3-41011 | * | 2/1991 | (JP) . |
| 99/53763 | * | 10/1999 | (WO) . |

OTHER PUBLICATIONS

Grace et al., Behavioural effects of a neem insecticide on Coptotermes formousanus (Isoptera: Rhinotermitidae), Tropical Pest Managment, vol. 38, No. 2, p. 176–180, 1992.*

Kawaguchi et al. (Abstract), JP403041011A, Controlling Agent of Termite, APS online, file JPO, Feb. 1991.*

Bobles (Abstract), DE 3912059, Controlling wood damaging insects with neem oil, WEST online file Derwent, Apr. 1992.*

Patel et al., Bioefficacy of Some Plant Products Against Mustard Saw Fly, Armyworm and Diamond Back Moth, Indian Journal of Plant Protection, vol. 21, No. 2, pp. 240–241, 1993.*

Sanyal et al., J Plant Anat Morphol (JODHPUR) 3 (1), pp. 13–19 (1986).

Ayoub et al., International Journal of Crude Drug Research, vol. 24, No. 1, pp. 16–18 (1986).

Dictionary of Microbiology and Molecular Biology, second edition. (1994), pp. 870, 504.

N.E. McIndoo, Plants of Possible Insecticidal Value, USDA, p. 128 (1945).

* cited by examiner

Primary Examiner—Jose' G. Dees
Assistant Examiner—Frank Choi
(74) Attorney, Agent, or Firm—Stradling Yocca Carlson & Rauth

(57) ABSTRACT

Disclosed are novel methods for a protecting or preserving wood, wood composites and other cellulosic materials, and in addition, disrupting the feeding behavior and growth cycle of termites, wood-borers and other insects, by applying certain compositions thereto which contain azadirachtin carried in neem tree extracts. Disclosed are novel neem extract compositions for coating, penetrating, treating, and curing said cellulosic materials which are non-toxic and provide long active lifetimes. The compositions contain the neem extracts in combination with binding and bittering agents which enhance the effectiveness of the extracts. The compositions are made from natural, active ingredients and are water resistant. The compositions are found to be non-reactive and non-toxic to vertebrates and non-polluting of surrounding soils. When used as intended in non-aerobic applications, the compositions are resistant to oxidation and ozonation. In addition, when used as intended in areas without sunlight, i.e. subterranean or concealed use, the compositions are not subject to UV and photo degradation.

23 Claims, No Drawings

METHOD FOR USING NEEM EXTRACTS AND DERIVATIVES FOR PROTECTING WOOD AND OTHER CELLULOSIC COMPOSITES

CROSS-REFERENCE TO RELATED APPLICATION

Not Applicable.

STATEMENT RE: FEDERALLY SPONSORED RESEARCH AND DEVELOPMENT

Not Applicable.

BACKGROUND OF THE INVENTION

Neem seeds, oil, leaves and twig sap have been used for medicinal and therapeutic purposes in treating or preventing ailments relating to the alimentary canal, ulcers, diabetes, skin, gums, teeth and hair. The neem leaves, when mixed with earth mortar, have been used in flooring and plastering of walls containing twigs and vines that act as reinforcement. The leaves have been known to protect the organically rich soil and the reinforcement for a considerable amount of time.

With the isolation of azadirachtin from the oil of neem seeds, it has been observed that azadirachtin—a tetranortriterpenoid having a molecular weight of 720.23—is the active ingredient that is a highly effective insect feeding deterrent. Various neem seed extracts, particularly those containing azadirachtin, are now known to influence the feeding behavior, growth regulation, and fecundity of numerous species of insects and fungi. Currently, azadirachtin is being investigated for prospective use as a biodegradable, non-toxic pesticide.

The prior art is replete with teachings of azadirachtin or azadirachtin-containing neem extracts, and methods of preparing the same, for use as pesticides. Azadirachtin and azadirachtin-containing neem extracts are desirable as pesticides in that they are non-toxic to humans and the environment. What is currently lacking in this art is ways in which to expand the uses of this environmentally safe, non-toxic insecticide.

Heretofore, for example, the use of neem extracts in compositions suitable for protecting wood and other cellulosic materials from infestation and destruction by termites, wood borers and other insects is unknown in the art.

Moreover, it is heretofore unknown in the art to use neem leaf paste in a composition suitable for protecting and preserving wood and other cellulosic materials from infestation and destruction by termites, wood borers and other insects.

Another shortcoming of azadirachtin is its stability i.e., it has a relatively short shelf life. The prior art discloses various attempts at retarding the degradation of azadirachtin. These prior art attempts typically involve extraction of the azadirachtin through the use of solvents at elevated temperatures and/or pressures. The current invention and applications preserve the efficacy of azadirachtin and avoid the precursors to degradation which result in loss of efficacy.

The invention preserves the efficacy of the azadirachtin in the neem plant extract by adding preservative, binding agents, in quantities above that naturally present in the neem plant extracts. These binding agents, lignins and tannins, are used individually or in combination to preserve the azadirachtin.

Lignin is a natural phenolic polymerie substance that is found in the cell walls of plant material. Lignin is extremely resistant to chemical and enzymic degradation, and it is not soluble in ordinary solvents unless it is degraded. Consequently, lignin is not readily biodegradable, impedes lytic actions of solvents in a wide range of pH levels, and provides corrosion resistance properties.

The melting point of lignin is measured around 250–275° Celsius, depending on the contact isomers. Lignins formed from the soda process, a common process in the field, are observed to have a lower melting range and offer better flow properties. Calcium lignosulfonate, a lignin derivative, is capable of polymerization under heat, which makes it useful in autoclaving for the cementing of the penetrated compositions and/or mixtures.

Tannin is a generic name for a family of weak polyphenolic acids that occur in the bark, woody tissues, and leaves of certain plants. In plants, tannins are believed to provide resistance to disease by binding to and reducing the availability of proteins in damaged plant tissue. Tannins tend to polymerize into insoluble compounds. There are two main types of tannins, namely pyrogallol tannins and catechol tannins. Catechol tannins exhibit significantly higher resistance to heat and decay than the pyrogallol tannins. Thus, catechol tannins have been used to protect fishing nets, sails, and leather goods against rotting and degrading under wet weathering.

Heretofore, the use of neem extracts in combination with additive concentrations of lignin or tannins for any purpose is unknown in the art, and in particular for protecting wood composites and other cellulosic materials from infestation and destruction by termites, wood borers and other insects. The additive quantities of Lignin and Tannin far exceed the naturally occurring quantities the neem plant or any other wood. The prior art does not teach the use of these components in combination for the preservation of wood composites and other cellulosic materials. The synergistic effects of these components used in combination are multiple, namely:

a) The broader antimicrobicidal activity;

b) The prolonged effective shelf and active life;

c) The improvement of basic properties, viz a viz, adhesion and water resistance.

The compositions described are applicable to softwood lumber and plywood for use in light commercial and residential foundations. The compositions work within the confines of the basic material and construction requirements, which are found in the design and fabrication of permanent wood foundation systems. The compositions offer coating, encapsulation, covering, barrier formation and preservation functions aside from the functions of the medium transporting the composition, i.e., paint, stain, caulk, or paste.

The compositions may be applied on foundation quality softwood lumber such as Fir, Pine, Ponderosa Pine, Red Pine, Western Hemlock and plywoods composed of softwood plies with exterior glue. For pressure treating lumber, the necessary preconditioning procedures may be carried out with the compositions.

These compositions are novel through their unique selection and combination of ingredients. No other combination disclosed in the prior art has achieved the qualities that the presently disclosed combinations have achieved, i.e. water resistance, resistance to oxidation and ozonation, resistance to UV and photo degradation, and a long effective life.

BRIEF SUMMARY OF THE INVENTION

The present invention relates to methods for protecting and preserving wood and other cellulose composites from termites and other insects by applying certain compositions of extracts and derivatives of the neem plant. The present invention also relates to these novel compositions so applied in which unique anti-feedant and preservative effects have been detected, as well as long effective life.

The compositions are made from natural, active ingredients and are water resistant. The compositions are found to be non-reactive and non-toxic to vertebrates and non-polluting of the surrounding soils. The compositions contain no high purity and expensive extractives. When used as intended in non-aerobic applications, the compositions are resistant to oxidation and ozonation. In addition, when used as intended in areas without sunlight, i.e. subterranean or concealed use, the compositions are not subject to UV and photo degradation.

The invention is directed toward the use of neem seed oil and neem leaf paste, either singly or in combination with each other or with other bittering and binding agents, as the active insect control agent in treatments applied to wood and wood composites. The synergistic effect of applying the neem extracts in combination with added amounts of binding and bittering agents, such as lignin and/or tannin, produces enhanced preservative effects against a wider variety of insects and for a longer effective life than is present or suggested in the prior art.

Novel methods and compositions of neem extracts, oil, and leaf paste concentrate are disclosed which not only result in a protectorant or preservative for wood, wood composites and other cellulosic materials, but also disrupt the feeding behavior and growth cycle of termites, wood-borers and other insects. When submerged in soils or otherwise exposed to water, the novel compositions so used and applied are generally insoluble in water and therefore provide long-lasting protection of the cellulosic materials.

Therefore, it is an object of this invention to disclose novel methods of protecting wood, wood compositions, and other cellulosic material utilizing new and effective compositions of neem extracts. A further object of this invention is to disclose novel methods and compositions involving combinations of neem plant extracts fortified with additional concentrations of binding agents such as lignin and tannin, for the synergistic effect of improved protection from environmental forces. Accordingly, it is an object of this invention to provide novel azadirachtin-containing formulations, including neem leaf paste compositions and other agents, for preserving and protecting wood, wood composites and other cellulosic materials. It is a further object of the instant invention to provide formulations which both inhibit infestation and act as a protectorant for wood materials and the like.

BRIEF DESCRIPTION OF THE DRAWINGS

Not Applicable.

DETAILED DESCRIPTION OF THE INVENTION

The instant invention is directed to novel methods of treating and preserving wood, wood composites and other cellulosic products which are substantially free of azadirachtin. Possible uses of the inventive methods include with lumber exposed directly or indirectly to soil, with lumber concealed from sunlight but still exposed to water, and with lumber other similar environments. The use of the inventive methods involves applying certain novel compositions including neem oil and neem leaf paste, used singly or in combination. The compositions also include binders, dispersing agents and other conventional wood preservatives, such as tannin and lignin, and act as preservatives and insecticides.

The compositions described are applicable to softwood lumber and plywood for use in light commercial and residential foundations. The compositions work within the confines of the basic material and construction requirements, which are found in the design and fabrication of permanent wood foundation systems. The compositions offer coating, encapsulation, covering, barrier formation and preservation functions aside from the functions of the medium transporting the composition, i.e., paint, stain, caulk, or paste.

The compositions may be applied on foundation quality softwood lumber. Examples of types of lumber include but are not limited to Fir, Pine, Ponderosa Pine, Red Pine, Western Hemlock and plywoods composed of softwood plies with exterior glue. For pressure treating lumber, the necessary preconditioning procedures may be carried out with the compositions.

These compositions are novel through their unique selection and combination of ingredients. The compositions are made from natural, active ingredients and are water resistant. The compositions are found to be non-reactive and non-toxic to vertebrates and non-polluting of the surrounding soils. The compositions contain no high purity and expensive extractives. When used as intended in non-aerobic applications, the compositions are resistant to oxidation and ozonation. In addition, when used as intended in areas without sunlight, i.e. subterranean or concealed use, the compositions are not subject to UV and photo degradation.

No other combination disclosed in the prior art has achieved the qualities that the presently disclosed combinations have achieved, i.e. water resistance, resistance to oxidation and ozonation, resistance to UV and photo degradation, and a long effective life. These combinations are novel in both their properties and in the unique selection and combination of components.

The neem oil and neem leaf paste contain azadirachtin. The efficacy of the azadirachtin-containing neem oil and neem leaf paste against termites, wood-borers and other insects, is utilized by coating, covering, encapsulating, penetrating, treating and otherwise applying same to wood, lumber and cellulosic composites thereby protecting said cellulosic material. The neem extract is either thick and viscous or thinned according to the preferred application, and remains generally insoluble in water so that the composition has a longer active life than the compositions in the prior art. This is accomplished by not isolating the extract, but rather fortifying the extract with binding agents and natural bitters, such as lignin and tannins.

The present invention applies well-known ingredients in combinations and concentrations not otherwise occurring naturally, and in areas and under circumstances not previously used or even suggested by the prior art. In the present invention, the azadirachtin is not isolated from the neem oil or neem leaf paste. Consequently, this active agent has a longer shelf life and active life than the prior art, and the compositions so made are non-reactive or otherwise toxic to the surrounding soil and environment.

The process for preparing stable neem leaf paste is a novel open to atmosphere, no heat process which includes the following steps:

1) classifying and de-matting neem leaves in bundles (leaves used for this purpose should be of a moisture content of not less than the critical moisture content);
2) washing and straining to remove dirt, rocks and other inert matter;
3) crushing and grinding to open up the effective surface area of the active plant material;

4) wet milling;

5) straining; and 6) homogenizing with neem oil and an emulsifier.

The resulting particle size distribution is in the range of approximately ten (10) microns to one (1) millimeter. The homogenized neem leaf paste is used as the active ingredient in caulks, joinery pastes and coating for lumber and other construction materials that come into direct or indirect contact with the earth. Preferably, the application comprises the neem leaf paste in an amount ranging from approximately 10% to 25% by weight of the overall composition.

Other compositions which have been found useful in the methods of the present invention include neem seed oil in combination with cross-linking or binding agents, such as lignin or tannin; extenders or bulk builders for structural rigidity, such as creosote and other resins; bittering agents, such as tannin; emulsifying agents; and/or transporting components, such as linseed oil. Lignin sulfonic acids and sulfonates are added to certain compositions to aid as emulsifying agents. The lignins and tannins, in the present invention, also have been found to be effective at producing a high degree of homogeneity in the overall composition by coalescing with the binding resins and the oils, as well as being effective at extending the coatings.

The following examples are provided to illustrate various suggested formulations of the neem extract composition for specified functions in accordance with the instant invention. These examples are not intended to be construed as limiting the invention in any way except as indicated in the appended claims. All percentages are by weight and are intended as approximations only and are provided herein for the clarity of the purposes and methods necessary for such applications.

EXAMPLE 1

For caulks, joinery pastes and coatings for lumber and other construction materials:

| | |
|---|---|
| Water Reducible Acrylic-Alkyd Copolymer | 20–40% |
| Methyl Methacrylate Fixative Resin | 1–5% |
| De-ionized or distilled Water | 15–35% |
| Neem Paste Emulsion | 5–25% |
| Neem Oil | 3–15% |
| Emulsifier | 1–5% |
| 2-Amino-2-Methyl-1-Propanol | 1–5% |
| Epoxified Sesame Oil | 4–10% |

The above ingredients are homogenized into a composition that results in the consistency of an extrudable paste.

EXAMPLE 2

For impregnating and coating treated/dry lumber for termite and wood borer protection:

| | |
|---|---|
| Creosote Oil | 25–50% |
| Lignin | 20–50% |
| Neem Seed Oil | 3–15% |
| Hydroquinone (as antioxidant for Neem Oil) | 1–3% |

The above ingredients are thoroughly blended without entrapping air, to result in a free flowing oil consistency.

EXAMPLE 3

For painting raw lumber for construction of foundation:

| | |
|---|---|
| Lignin | 5–20% |
| Creosote Coal Tar Solution | 55–85% |
| Neem Seed Oil | 4–20% |

The above ingredients are thoroughly blended without entrapping air, to result in a liquid with the consistency of a brushable paint.

EXAMPLE 4

For coating construction lumber:

| | |
|---|---|
| Vinylpyrollidone Styrene Copolymer | 10–30% |
| De-ionized water | 20–45% |
| 2-Amino-2-Methyl-1-Propanol | 1–5% |
| Neem seed oil in water emulsion | 4–20% |
| Emulsifying agent (e.g., Lignin Sulfonic Acid or Lignin Sulfate) | 1–5% |
| Aqueous Dispersion pigment (of color choice) | 1–5% |
| Epoxified linseed oil | 1–8% |

The above ingredients are thoroughly blended without entrapping air, to result in a liquid with the consistency of a brushable paint.

EXAMPLE 5

For coating, painting and joining of construction lumber:

| | |
|---|---|
| Vinylpyrollidone styrene copolymer | 15–35% |
| De-ionized water | 25–50% |
| 2-Amino-2-Methyl-1-Propanol | 1–5% |
| Neem seed oil in water emulsion | 4–20% |
| Water Reducible Acrylic/medium oil alkyd resin | 5–20% |
| Emulsifying agent | 1–5% |
| Aqueous Pigment dispersion | 1–5% |
| Epoxified linseed oil | 1–8% |

As an alternative to vinylpyrollidone styrene copolymer, polyvinylpyrolidone vinylacetate copolymer may be used.

The above ingredients are intimately homogenized to result in thin consistency, brushable paint.

EXAMPLE 6

For treating lumber:

| | |
|---|---|
| Tung oil | 25–45% |
| Lignin oil | 25–45% |
| Neem seed oil | 4–20% |
| Asphaltum | 2–10% |
| Epoxified linseed oil | 1–5% |
| Hydroquinone (as antioxidant for Neem Oil) | 1–3% |

The above ingredients are mixed thoroughly without entrapping air to result in a free flowing oil.

EXAMPLE 7

For Barrier Paste compositions for coating subterranean wood and lumber:

| | |
|---|---|
| Teak Saw dust, particle size avg. (40 to 100 mesh, slow-dried below 850 Fahrenheit) | 5–25% |
| Long oil Alkyd resin | 10–25% |
| Neem Oil | 4–20% |
| Complex butyl methyl phenol | 0–5% |
| Pentasodium Salt of Diethylenetriamine-penta-acetic Acid | 0–5% |
| Styrenated Linseed Oil | 20–35% |
| Catechol Tannin | 3–8% |

The above ingredients are blended thoroughly without entrapping air to yield a composition having the consistency of an extrudable paste.

EXAMPLE 8

For impregnating and dry-autoclaving of wood and lumber:

| | |
|---|---|
| Neem seed oil | 15–40% |
| Styrenated Linseed oil | 30–60% |
| Catechol Tannin complex butyl | 3–8% |
| Methyl Phenol | 1–10% |
| Teak wood oil | 1–8% |

The above ingredients are blended thoroughly without entrapping air to result in a free flowing, sprayable oil composition.

Preferably, as shown above, the neem seed oil is used in an amount ranging from approximately 3% to 40%, by weight, of the composition depending upon the specific application or treatment. Also, as so formulated, these compositions are generally water insoluble, non-acidic and non-reactive, having pH levels ranging from about 6.0 and greater. These combinations of active and inactive ingredients produce synergistic effects that have not been exploited in the field, nor have they been suggested by the prior art. This synergism displays enhanced preservative effects over a wider range of insect and environmental forces for a longer active lifetime and stability than anything presented in the prior art.

The methods and compositions in the present invention are superior to and represent significant improvements over the prior art in that the methods and compositions disclosed herein provide long lasting protection of wood and other cellulosic materials from termites and other wood boring insects. These compositions are generally insoluble in water, non-acidic and non-reactive. Thus, the compositions, as applied to wood and exposed to soil or other environments permitting exposure to water, are not readily removed or diluted through such water exposure. Furthermore, the compositions are generally non-toxic to the soil and environment.

The composition acts effectively for an extended period of time as a result of the locations in which the compositions are applied, where there is a lack of oxidative, ozonative and ultraviolet radiative precursors to degradation. The oily nature of the coatings and compositions prevents the hydrolytic weathering of bonded and cured material.

The above-described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method of treatment for protecting and preserving lumber comprising:
    a) providing a lumber substrate substantially free of azadirachtin;
    b) treating the lumber substrate by applying a composition comprising:
        (i) an amount of azadirachtin sufficient to protect and preserve the lumber substrate from infestation and destruction by insects, which azadirachtin is contained in a neem plant material extract; and
        (ii) a lignin substance, a tannin compound or mixture thereof, the amount of which is in addition to that naturally present in the neem plant material extract and sufficient to preserve the neem plant material extract and azadirachtin contained therein from degradation;
    wherein the composition coats the exposed surface of the lumber substrate to be protected and a minimal portion of the composition is absorbed into the lumber substrate; and
    c) curing the treated lumber substrate.

2. A The method according to claim 1 wherein the lignin substance is in an amount ranging from 1% to 50% by weight of the composition, in addition to that naturally present in the neem plan material extract.

3. The method according to claim 2 wherein the lignin substance is selected from the group consisting of Lignin, Lignin Sulfonic Acid, Lignin Sulfate and Lignin Oil.

4. The method according to claim 1 wherein the tannin compound is in an amount ranging from 3% to 8% by weight of the composition, in addition to that naturally present in the neem plant material extract.

5. The method according to claim 4 wherein the tannin compound is selected from the group consisting of Catechol Tannin and Catechol Tannin complex butyl.

6. A composition for protecting and preserving lumber where the lumber is substantially free of azadirachtin comprising:
    a) sufficient amount of neem plant material extract wherein said sufficient amount of a neem plant material extract provides an amount of azadirachtin sufficient to protect and preserve the lumber from infestation and destruction by insects;
    b) sufficient amount of a binding agent selected from the group consisting of a lignin substance, a tannin compound and mixtures thereof, the amount of which is in addition to that naturally present in the neem plant material extract and sufficient to preserve the neem plant material extract and the azadirachtin contained therein from degradation; and
    c) a bulk builder selected from the group consisting of creosotes, methyl methacrylics, water reducible acrylics and long oil alkyds.

7. The composition according to claim 6 wherein the binding agent is a lignin substance selected from the group consisting of Lignin, Lignin Sulfonic Acid, Lignin Sulfate, and Lignin Oil.

8. The composition according to claim 7 wherein the lignin substance is in an amount ranging from 1% to 50% by weight of the composition, in addition to that naturally present in the neem plant material extract.

9. The composition according to claim 6 wherein the binding agent is tannin compound selected from the group consisting of Catechol Tannin and Catechol Tannin complex butyl.

10. The composition according to claim 9 wherein the tannin compound is in an amount ranging from 3% to 8% by weight of the composition, in addition to that naturally present in the neem plant material extract.

11. The composition according to claim 6 further comprising an emulsifying agent selected from the group consisting of linseed oils, lignin sulfonic acids, lignin sulfates, and sulfonates.

12. The composition according to claim 6 further comprising a carrier selected from the group consisting of water reducible acrylic/alkyd copolymers, 2-amino-2-methyl-1-propanol, vinylpyrrolidone styrene copolymers, and methyl methacrylate fixative resin.

13. A composition for protecting and preserving lumber where the lumber is substantially free of azadirachtin comprising:
   a) sufficient amount of a neem plant material extract wherein said sufficient amount of a neem plant material extract provides an amount of azadirachtin sufficient to protect and preserve the lumber from infestation and destruction by insects;
   b) sufficient amount of a binding agent selected from the group consisting of a lignin substance, a tannin compound and mixtures thereof, the amount of which is in addition to that naturally present in the neem plant material extract and sufficient to preserve the neem plant material extract and the azadirachtin contained therein from degradation;
   c) a bulk builder selected from the group consisting of creosotes, methyl methacrylics, water reducible acrylics and long oil alkyds; and
   d) a carrier selected from the group consisting of water reducible acrylic/alkyd copolymers, 2-amino-2-methyl-1-propanol, vinylpyrrolidone styrene copolymers, and methyl methacrylate fixative resin.

14. The composition according to claim 13 wherein the binding agent is lignin substance selected from the group consisting of Lignin, Lignin Sulfonic Acid, Lignin Sulfate, and Lignin Oil.

15. The composition according to claim 14 wherein the lignin substance is in an amount ranging from 1% to 50% by weight of the composition, in addition to that naturally present in the neem plant material extract.

16. The composition according to claim 13 wherein the binding agent is a tannin compound selected from the group consisting of Catechol Tannin and Catechol Tannin complex butyl.

17. The composition according to claim 16 wherein the tannin compound is in an amount ranging from 3% to 8% by weight of the composition, in addition to that naturally present in the neem plant material extract.

18. The composition according to claim 13 wherein said lignins and tannins also act as a bittering agent.

19. An improved insect resistant lumber comprising:
   a) a piece of lumber that is substantially free of azadirachtin;
   b) said lumber having been treated by a sufficient amount of a neem plant material extract wherein said sufficient amount of a neem plant material extract provides an amount of azadirachtin sufficient to protect and preserve the lumber from infestation and destruction by insects; and
   c) a sufficient amount of a binding agent selected from the group consisting of a lignin substance, a tannin compound and mixtures thereof, the amount of which is in addition to that naturally present in the neem plant material extract and sufficient to preserve the neem plant material extract and the azadirachtin contained therein from degradation.

20. The insect resistant lumber according to claim 19 wherein the binding agent is a lignin substance which is present in an amount ranging from 1% to 50% by weight of the composition, in addition to that naturally present in the neem plant material extract.

21. The insect resistant lumber according to claim 19 wherein the lignin substance is selected from the group consisting of Lignin, Lignin Sulfonic Acid, Lignin Sulfate, and Lignin Oil.

22. The insect resistant lumber according to claim 19 wherein the binding agent is a tannin compound which is present in an amount ranging from 3% to 8% by weight of the composition, in addition to that naturally present in the neem plant material extract.

23. The insect resistant lumber according to claim 19 wherein the tannin compound is selected from the group consisting of Catechol Tannin complex butyl.

\* \* \* \* \*